United States Patent
van Lengerich

(10) Patent No.: US 7,201,923 B1
(45) Date of Patent: Apr. 10, 2007

(54) ENCAPSULATION OF SENSITIVE LIQUID COMPONENTS INTO A MATRIX TO OBTAIN DISCRETE SHELF-STABLE PARTICLES

(75) Inventor: Bernhard H. van Lengerich, Plymouth, MN (US)

(73) Assignee: General Mills, Inc., Minneapolis, MN (US)

( * ) Notice: Subject to any disclaimer, the term of this patent is extended or adjusted under 35 U.S.C. 154(b) by 0 days.

(21) Appl. No.: 09/233,443

(22) Filed: Jan. 20, 1999

Related U.S. Application Data

(60) Provisional application No. 60/109,696, filed on Nov. 24, 1998, provisional application No. 60/103,700, filed on Oct. 9, 1998.

(51) Int. Cl.
 *A61K 9/14* (2006.01)
 *A61K 47/36* (2006.01)
(52) U.S. Cl. .................................. 424/499; 424/488
(58) Field of Classification Search ................ 424/484, 424/488, 493, 499; 426/516, 96, 560; 427/2.14, 427/214
 See application file for complete search history.

(56) References Cited

U.S. PATENT DOCUMENTS

| | | | |
|---|---|---|---|
| 2,876,160 A | | 3/1959 | Schoch et al. |
| 3,027,102 A | | 3/1962 | Lödige et al. |
| 3,404,984 A | | 10/1968 | Olsen |
| 3,762,931 A | * | 10/1973 | Craig et al. |
| 3,786,123 A | | 1/1974 | Katzen |
| 3,868,471 A | | 2/1975 | Decelles et al. |
| 3,922,354 A | | 11/1975 | Galluzzi et al. |
| 3,925,343 A | * | 12/1975 | Hampton et al. |
| 3,928,567 A | * | 12/1975 | Andersen et al. |
| 3,962,416 A | | 6/1976 | Katzen |
| 3,992,555 A | | 11/1976 | Kovacs |
| 4,075,356 A | | 2/1978 | Haag et al. |
| 4,106,991 A | | 8/1978 | Markussen et al. |
| 4,178,392 A | | 12/1979 | Gobble et al. |
| 4,187,321 A | | 2/1980 | Mutai et al. |
| 4,242,219 A | | 12/1980 | Bogerman et al. |
| 4,379,171 A | | 4/1983 | Furda et al. |
| 4,386,106 A | | 5/1983 | Merritt et al. |
| 4,532,145 A | | 7/1985 | Saleeb et al. |
| 4,689,235 A | | 8/1987 | Barnes et al. |
| 4,816,259 A | | 3/1989 | Matthews et al. |
| 4,871,574 A | | 10/1989 | Yamazaki et al. |
| 4,886,820 A | | 12/1989 | Gross et al. |
| 4,888,171 A | | 12/1989 | Okonogi et al. |
| 4,895,725 A | | 1/1990 | Kantor et al. |
| 4,999,208 A | | 3/1991 | Lengerich et al. |
| 5,009,900 A | | 4/1991 | Levine et al. |
| 5,023,083 A | | 6/1991 | Drell |
| 5,064,669 A | | 11/1991 | Tan et al. |
| 5,071,668 A | | 12/1991 | van Lengerich et al. |
| 5,074,902 A | * | 12/1991 | Connick, Jr. et al. |
| 5,075,058 A | | 12/1991 | Chan et al. |
| 5,079,012 A | | 1/1992 | Lengerich et al. |
| 5,087,461 A | | 2/1992 | Levine et al. |
| 5,106,639 A | | 4/1992 | Lee et al. |
| 5,118,513 A | | 6/1992 | Mehansho et al. |
| 5,183,690 A | | 2/1993 | Carr et al. |
| 5,262,167 A | * | 11/1993 | Vegesna et al. |
| 5,296,000 A | | 3/1994 | Darmont et al. |
| 5,314,692 A | | 5/1994 | Haarasilta et al. |
| 5,320,669 A | * | 6/1994 | Lim et al. |
| 5,431,929 A | | 7/1995 | Yatka et al. |
| 5,458,823 A | | 10/1995 | Perkins et al. |
| 5,466,460 A | | 11/1995 | McMahon et al. |

(Continued)

FOREIGN PATENT DOCUMENTS

DE 37 38 042 A 5/1988

(Continued)

OTHER PUBLICATIONS

Per Artusson et al., "Characterization of Polyacryl Starch Microparticles as Carriers for Proteins and Drugs," *Journal of Pharmaceutical Science*, vol. 73, No. 11, pp. 1507-1513 (Nov. 1984).

(Continued)

*Primary Examiner*—Edward J. Webman
(74) *Attorney, Agent, or Firm*—Douglas J. Taylor; Barry I. Hollander; John A. O'Toole

(57) ABSTRACT

A liquid encapsulant component which contains an active, sensitive encapsulant, such as a live microorganism or an enzyme dissolved or dispersed in a liquid plasticizer is admixed with a plasticizable matrix material. The matrix material is plasticizable by the liquid plasticizer and the encapsulation of the active encapsulant is accomplished at a low temperature and under low shear conditions. The active component is encapsulated and/or embedded in the plasticizable matrix component or material in a continuous process to produce discrete, solid particles. The liquid content of the liquid encapsulant component provides substantially all or completely all of the liquid plasticizer needed to plasticize the matrix component to obtain a formable, extrudable, cuttable, mixture or dough. Removal of liquid plasticizer prior to extrusion is not needed to adjust the viscosity of the mixture for formability. Release of an active component from the matrix may be delayed or controlled over time so that the active component is delivered when and where it is needed to perform its intended function. Controlled release, discrete, solid particles which contain an encapsulated and/or embedded component such as a heat sensitive or readily oxidizable pharmaceutically, biologically, or nutritionally active component are continuously produced without substantial destruction of the matrix material or encapsulant.

22 Claims, No Drawings

U.S. PATENT DOCUMENTS

| | | | |
|---|---|---|---|
| 5,508,053 A | 4/1996 | Villota et al. |
| 5,514,387 A | 5/1996 | Zimmerman et al. |
| 5,567,730 A | 10/1996 | Miyashita et al. |
| 5,597,416 A | 1/1997 | Fuisz et al. |
| 5,683,720 A | 11/1997 | Myers et al. |
| 5,716,615 A * | 2/1998 | Cavaliere-Vesely et al. |
| 5,744,180 A | 4/1998 | Cherukuri et al. |
| 5,750,104 A | 5/1998 | Sipos |
| 5,820,903 A | 10/1998 | Fleury et al. |
| 5,851,553 A | 12/1998 | Myers et al. |
| 5,862,998 A | 1/1999 | Bogue et al. |
| 5,894,029 A * | 4/1999 | Brown et al. |
| 5,902,617 A | 5/1999 | Pabst |
| 5,939,127 A | 8/1999 | Abboud |
| 5,952,033 A | 9/1999 | Anantharaman et al. |
| 5,958,502 A | 9/1999 | Fulger et al. |
| 5,972,373 A | 10/1999 | Yajima et al. |
| 5,972,395 A | 10/1999 | Saleeb et al. |
| 5,972,404 A | 10/1999 | van Lengerich |
| 5,972,415 A | 10/1999 | Brassart et al. |
| 5,976,603 A | 11/1999 | Kota et al. |
| 6,004,594 A | 12/1999 | van Lengerich |
| 6,008,027 A | 12/1999 | Langner |
| 6,024,994 A | 2/2000 | Jacobson et al. |
| 6,048,551 A | 4/2000 | Hilfinger et al. |
| 6,149,965 A | 11/2000 | van Lengerich et al. |
| 6,168,811 B1 | 1/2001 | Clark et al. |
| 6,174,553 B1 | 1/2001 | Cerda et al. |
| 6,190,591 B1 | 2/2001 | van Lengerich |
| 6,242,033 B1 | 6/2001 | Sander |
| 6,261,613 B1 | 7/2001 | Narayanaswamy et al. |
| 6,284,268 B1 | 9/2001 | Mishra et al. |
| 6,342,257 B1 | 1/2002 | Jacobson et al. |
| 6,368,621 B1 | 4/2002 | Engel et al. |
| 6,436,453 B1 | 8/2002 | van Lengerich et al. |
| 6,468,568 B1 | 10/2002 | Leusner et al. |
| 6,500,463 B1 | 12/2002 | van Lengerich |
| 2001/0008635 A1 | 7/2001 | Quellet et al. |
| 2001/0044026 A1 | 11/2001 | Vaghefi et al. |

FOREIGN PATENT DOCUMENTS

| | | |
|---|---|---|
| DE | 40 21 678 | 1/1992 |
| DE | 40 41 752 A1 | 6/1992 |
| EP | 33662 A | 10/1969 |
| EP | 47014316 A | 10/1972 |
| EP | 0 202 408 A2 | 11/1986 |
| EP | 0 223 963 A | 6/1987 |
| EP | 0 347 014 A1 | 12/1989 |
| EP | 0 385 081 A2 | 9/1990 |
| EP | 391518 A | 10/1990 |
| EP | 0 462 012 A2 | 12/1991 |
| EP | 0 465 364 A1 | 1/1992 |
| EP | 552057 A | 7/1993 |
| EP | 603992 A1 | 6/1994 |
| EP | 605913 A | 7/1994 |
| EP | 0 705 541 A1 | 4/1996 |
| EP | 1064 856 A2 | 1/2001 |
| EP | 1066 761 A2 | 1/2001 |
| EP | 1 118 274 A | 7/2001 |
| FR | 2 640 472 A | 6/1990 |
| FR | 2 758 055 | 7/1998 |
| GB | 15312 | 0/1911 |
| GB | 1 437 501 A | 5/1976 |
| JP | 59139317 A | 8/1984 |
| JP | 63 173568 | 7/1988 |
| JP | 1313421 A | 12/1989 |
| JP | 6024962 A | 2/1994 |
| JP | 2000139372 A | 5/2000 |
| WO | WO 85/04074 | 9/1985 |
| WO | WO 88/01512 A | 3/1988 |
| WO | WO 90/15537 | 12/1990 |
| WO | 91 03940 | 4/1991 |
| WO | WO 92/00130 | 1/1992 |
| WO | WO 92/00140 | 1/1992 |
| WO | WO 92/12645 | 8/1992 |
| WO | WO 94/01001 | 1/1994 |
| WO | WO 94/23593 | 10/1994 |
| WO | WO 95/00121 | 1/1995 |
| WO | WO 95/18544 | 7/1995 |
| WO | WO 95/26752 | 10/1995 |
| WO | 96 09773 | 4/1996 |
| WO | 96 14058 | 5/1996 |
| WO | WO 97/16076 | 5/1997 |
| WO | WO 97/38016 A | 10/1997 |
| WO | WO 97/39116 | 10/1997 |
| WO | WO 98/02148 A | 1/1998 |
| WO | WO 98/09981 A | 3/1998 |
| WO | WO 98/18610 | 5/1998 |
| WO | WO 98/35704 A | 8/1998 |
| WO | WO 98/50019 A | 11/1998 |
| WO | WO 98/54980 | 12/1998 |
| WO | WO 98/58642 A | 12/1998 |
| WO | WO 99/11242 A1 | 3/1999 |
| WO | WO 99/20745 A1 | 4/1999 |
| WO | WO 99/45904 A1 | 9/1999 |
| WO | WO 99/56563 | 11/1999 |
| WO | WO 99/61002 A1 | 12/1999 |
| WO | WO 00/41740 A2 | 7/2000 |
| WO | WO 00/64436 A1 | 11/2000 |
| WO | WO 01/74175 A1 | 10/2001 |

OTHER PUBLICATIONS

Lennart Randen et al., "Coprecipitation of Enzymes with Water Soluble Starch—An Alternative to Freeze-drying," *J. Pharm. Pharmacol.*, vol. 40, pp. 763-766 (1988).

Shigeaki Maruo et al., "Effects of Moranoline, 4-*O*-β-D-Glucopyranosylmoranoline and Their *N*-Substituted Derivatives on Thermostability of Cyclodextrin Glycosyltransferase, Glucoamylase, and β-Amylase," *Biosci. Biotech. Biochem.*, vol. 57, No. 8, pp. 1294-1298., (1993).

Wendell Q. Sun et al., "Protein stability in the amorphous carbohydrate matrix: relevance to anhydrobiosis," *Biochimica et Biophysica Acta*, vol. 1425, pp. 245-254 (1998).

Colonna et al., "Extrusion Cooking of Starch & Starchy Products," *Extrusion Cooking*, C. Mercier, et al. AACC, St. Paul, MN (1989), pp. 247-319.

Meuser et al., "A Systems Analytical Approach To Extrusion," *Food Extrusion Science & Technology*, ed. J. Kokini, Dekker Publ. (1992), pp. 619-630.

Colonna et al., "Extrusion Cooking of Starch & Starchy Products," *Extrusion Cooking*, C. Mercier et al. AACC, St. Paul, MN (1989), pp. 247-319.

Meuser et al., "A System Analytical Approach To Extrusion," *Food Extrusion Science & Technology*, ed. J. Kokini, Dekker Publ. (1992), pp. 619-630.

Brochure entitled "Innovate With Raftiline®," Orafti Active Food Ingredients, Nov. 1996.

"Inulin-A 'Good-for-you' Fat Replacer, Texture Modifier," *Food Formulating*, p. 15, Feb. 1997.

Brighenti, F., et al., "One Month Consumption of Ready-to-eat Breakfast Cereal Containing Inulin Markedly Lowers Serum Lipids in Normolipidemic Men," from: Proceedings of 7th FENS European Nutritional Conference, Vienna, 1995.

Silva, R., "Use of Inulin as a Natural Texture Modifier," *Cereal Foods World*, Oct. 1996, vol. 41, No. 10, pp. 792-794.

Niness, "Breakfast Foods and the Health Benefits of Inulin and Oligofructose", *Cereal Foods World*, vol. 44, No. 2, Feb. 1999, pp. 79-81.

U.S. Appl. No. 11/263,360, filed Oct. 31, 2005, van Lengerich et al.

Hermann, "Specialty Dairy Ingredients", Food Product Design, Feb. 1992.

* cited by examiner

ENCAPSULATION OF SENSITIVE LIQUID COMPONENTS INTO A MATRIX TO OBTAIN DISCRETE SHELF-STABLE PARTICLES

RELATED APPLICATIONS

This application claims priority under 35 U.S.C. 119(e) of U.S. provisional application Nos. 60/103,700 filed on Oct. 9, 1998, and 60/109,696, filed on Nov. 24, 1998.

FIELD OF THE INVENTION

The present invention relates to a continuous process for producing shelf-stable, controlled release, discrete, solid particles from a liquid encapsulant component which contains a sensitive encapsulant, such as a heat sensitive or readily oxidizable pharmaceutically, biologically, or nutritionally active component.

BACKGROUND OF THE INVENTION

In encapsulating a component in a matrix, the matrix material is generally heated to a sufficiently high temperature to provide a plasticized mass which facilitates embedding or coating of the component. Upon cooling, the matrix material hardens or becomes solidified and protects the encapsulant from undesirable or premature reaction. However, heating of the matrix to plasticize it or to form a melt may deleteriously affect or decompose the encapsulant as well as the matrix material. Additionally, the mixing or high shear used to disperse the encapsulant uniformly throughout the plasticized matrix material may likewise adversely affect the matrix material or encapsulant. Furthermore, the use of high temperatures to plasticize or melt the matrix material may cause evaporation and loss of the encapsulant. The addition of liquids to the matrix material to reduce its viscosity and to facilitate mixing may require excessive drying or evaporation of the plasticizing liquid for the attainment of a formable composition capable of being formed into discrete, substantially uniform pieces. Furthermore, removal of the plasticizing liquid may adversely expand the product, decrease its density, and make the encapsulated component more susceptible to attack or more easily released. These problems involved with the removal of liquid encapsulant are even more pronounced when the commercially available form of the encapsulant is dissolved or dispersed in a liquid. While the liquid may be removed prior to encapsulation by drying, expensive methods such as spray drying, freeze drying, and vacuum drying are generally needed to avoid decomposition of the encapsulant by drying at elevated temperatures. Additionally, the dried encapsulants may be dusty and may cause adverse health effects when handled in concentrated forms or when inhaled.

The production of expanded products is disclosed in European patent publication nos. EP 0465364 A1 (published Jan. 8, 1992) and EP 0462012 A2 (published Dec. 18, 1991), U.S. Pat. No. 3,962,416 to Katzen and U.S. Pat. no. 3,786,123 to Katzen. The two European patent publications disclose the production of an anti-obesity food and a method for making it by extrusion of starches with fatty acids into an expanded product having densities between 0.1 and 0.3 g/cm$^3$. U.S. Pat. No. 3,962,416 to Katzen discloses an expanded product which contains at least one nutrient and one gelatinized starch.

U.S. Pat. No. 3,786,123 to Katzen discloses a method for producing encapsulated nutrients using extrusion temperatures of between 250° F. and 400° F. and extrusion pressures of between 200 psi to 2500 psi. A high protein encapsulating agent containing up to 40% starch may be used. The starch is is gelatinized and extruded into an expanded product.

However, in producing a product having controlled release or delayed release, excessive expansion or puffing may result in too rapid release properties or may undesirably expose an encapsulant to destructive reactions. For example, an edible composition for delivering encapsulated pharmaceutically or nutritionally active components or for a non-edible agricultural product for delivering biocides or herbicides, it is desirable that the products have a substantially spherical shape and a high density. Such products exhibit a substantially low ratio between surface area and volume and thus minimize or prevent surface related destructive reactions that occur upon exposure to air or oxygen and light. The spherical shapes and high densities also minimize the surface which would be available to expose embedded material which is not encapsulated. Furthermore, for edible products for delivering pharmaceutically or nutritionally active components, it is desirable that the products are capable of being consumed or swallowed without chewing or substantially no chewing. Avoiding the need for mastication, further assures that the products reach the digestive tract without substantial enzymatic hydrolysis in the mouth. Furthermore, it helps to control or reduce dissolution of the product in gastric juice and to control the release of the embedded or encapsulated components in the stomach and/or in the intestine.

International patent publication no. WO92/00130 (published Jan. 9, 1992) discloses a continuous process for obtaining an encapsulated, biologically active product in a starchy matrix. A biologically active agent and starch are mixed before extrusion and extruded as a blend, with the encapsulant or biologically active agent being heated together with the starch. Alternatively, a core material to be encapsulated may be added and blended with an aqueous dispersion of starch after the starch and water have been subjected to an elevated temperature sufficient to gelatinize the starch. The extrusion process, it is disclosed, exposes the mix to high shear mechanical action at a temperature above the gelatinization temperature of the starch. The use of extrusion barrel temperatures of between about 58° C. and 98° C. are disclosed. While these barrel temperatures may be above the gelatinization temperature of starch, the extruder utilized has barrel sections that are only three lid long. The screw speeds utilized, between 400 rpm and 200 rpm result in a very short residence time of the blend inside the extruder and barely allow heating up of the starch water mix. As a result, the temperatures obtained are generally too low to obtain substantial gelatinization of native starches. Additionally, the barrel temperatures used are particularly too low for substantial gelatinization of high amylose starch which generally gelatinizes at temperatures substantially above 100° C., for example at 125° C. The use of extrusion barrel temperatures which are not sufficiently high to substantially or completely gelatinize the starch may not form a sufficiently continuous, plasticized and homogeneous matrix for effective embedding or encapsulation.

In addition, the use of relatively low extrusion temperatures, high speed mixing, and a high viscosity starch composition generally requires a high mechanical energy input. High shear is directly related to high specific mechanical energy, which in turn increases the molecular destructurization and dextrinization of starch. Breakdown of the starch molecules, and in particular the amylopectin, increases the solubility of the extruded starch composition in aqueous systems as described in P. Colonna, et al., "Extrusion Cooking of Starch & Starchy Products," *Extrusion Cooking*, C. Mercier, et al. pp. 247–319, AACC, St. Paul, Minn. (1989) and F. Meuser, et al, "A Systems Analytical Approach To Extrusion," *Food Extrusion Science &Technology*, ed. J. Kokini, Dekker Publ., pp. 619–630 (1992). Increased solubility of the extruded starch in aqueous systems decreases the stability of the product against moisture and subsequently diminishes or shortens the protection and controlled release of the embedded or encapsulated substances. In addition, subjecting the encapsulant to the same high shear and high temperature conditions to which the starch is subjected may adversely affect the encapsulant by at least partially destroying it or decomposing it into unknown solid or volatile substances.

Pregelatinized starch is used in numerous applications in the food industry as a swelling agent and for accelerated and extended water absorption in foods such as soups, sauces, instant puddings, baby food, and thickening agents. However, it has been found that the use of pregelatinized starch or the use of starch as the only matrix material during extrusion cooking generally results in a matrix which releases the encapsulant too quickly. It has been found that the penetration of water into a pure starch matrix causes early release of the encapsulant into the environment. Generally the time to release 100% of the encapsulant is too short to provide a desirable time-release or controlled-release which is effective for delivering the encapsulant at a desired location or time.

International patent publication no. WO 95/26752 (published Oct. 12, 1995) discloses the production of a food product for the enteric supply of a fatty acid, a fatty acid containing substance, an amino acid, or an amino acid containing substance by at least partially complexing the fatty acid or amino acid in the amylose helix of starch to mask the acid. The product may contain one or more flavors and colors, fat soluble substances, anti-oxidants, or pharmacologically effective substances. The components may be first dry mixed and subsequently heated fed into an extruder where they are substantially mixed and subsequently heated above the gelatinization temperature of the starch to obtain an elasticized mass which is extruded and formed into pellets. However, heat-sensitive components would be destroyed during the heating step.

International patent publication no. WO 85/04074 to Flashinski, et al. a (published Sep. 26, 1985) discloses an insect bait containing an insect-controlling material in a gelatinized starch matrix. The bait is made by coextruding starch with the insect-controlling material at temperature and pressure conditions sufficient to cook and gelatinize the starch. Alternatively, a pregelatinized starch may be mixed with the insect-controlling material and water to form a gel. In the formation of the insect bait by mixing and extruding the components, it is disclosed, it is essential to utilize additives, including the insecticides and repellants which will withstand the extrusion temperatures of starch without the degradation or vaporization. The extrusion temperatures of the insect-bait mixture, depending upon the starch content and other additives, ranges between about 160 to about 310° F. at pressures of from about 300 through 800 psi.

U.S. Pat. No. 5,183,690 to Carr, et al. discloses a continuous process for imparting predetermined release properties to an encapsulated biologically active agent in a matrix of starchy material. The starchy material, an active agent, and water are continuously blended in an ingredient stream wherein the starchy material is at a solids concentration of at least 40%. The ingredients stream is continuously extruded as an extrudate and the extrudate is continuously recovered. The conditions of blending, extruding, and recovering are preselected to yield the predetermined release properties. The temperature is elevated to at least about 65° C. to effect gelatinization of starch and assure an essentially molecular dispersion of the starch in the water. Alternatively, the core material to be encapsulated is added and blended with the aqueous dispersion of starch after the starch and water has been subjected to an elevated temperature sufficient to gelatinize the starch. In this embodiment the aqueous starch stream containing gelatinized starch may be lowered to a temperature as low as about 25° C. before the core material to be encapsulated is added and subjected to high-shear mechanical action. Under such low temperature conditions of admixture it is disclosed, the activity of sensitive biological material, such as bacteria and viruses, is preserved and loss of volatile organic materials is minimized. The rate of swelling of the products in water and the rate of release of active agents are controlled by altering the amount of water present in the starch-agent-water blend during processing. As the amount of water is decreased, both the swelling rate and the release rate increase. The rate of swelling of the products in water and the rate of release of active agent are also controlled by passage of the extrudate containing starch-agent-water through an exit die of various dimensions. As the exit die is reduced in size, both the rate and extent of swelling increase and the rate of release of agent increases.

Copending international Patent Application No. PCT/US97/18984, filed Apr. 27, 1997 the name of Bernhard. Van Lengerich, and published under International Publication No. WO 98/18610 on May 7, 1998, the disclosures of which are herein incorporated by reference in their entireties, disclose a controlled release particulate composition which contains a hydrophobic component for controlling the release of an encapsulated and/or embedded active component from a plasticized matrix. High water binding capacity agents may also be used to delay or control the release of the encapsulant from the matrix. A high amount of plasticizer is employed to facilitate plasticization of the matrix material at low shear and is then reduced prior to adding the encapsulant to facilitate subsequent forming and to reduce post extrusion drying. The controlled release or delayed release composition may be produced without substantial expansion of the matrix material to thereby avoid production of a low density product which prematurely or too rapidly releases the encapsulant or the embedded component.

The present invention provides a process for producing discrete, particulate, shelf-stable encapsulated heat-sensitive components from solutions or dispersions of the component without the need for predrying of the solution or dispersion. The particulates may be produced at low temperatures to avoid thermal destruction of the heat-sensitive components and to avoid substantial expansion. An extrudable, formable, cuttable, mixture or dough may be obtained continuously without the need for removing or evaporating liquid plasticizer prior to extrusion or forming. The processes of the present invention may be used for the continuous production of an edible composition for delivering pharmaceutically or nutritionally active components, such as enzymes or live microorganisms, or the production of an agricultural product for the controlled release of biocides, herbicides, fertilizers, growth stimulators, pesticides, or products for other uses such as, for example, detergents which release chemical and/or biological agents.

SUMMARY OF THE INVENTION

The present invention provides a continuous process for producing controlled release, discrete, solid particles which contain an encapsulated and/or embedded component from a liquid encapsulant component. The particles comprise a matrix material in which the active component is encapsulated or embedded. The matrix material is plasticizable by the liquid of the liquid encapsulant component under low shear and low temperature conditions which are sufficiently low so as to avoid substantial decomposition, destruction, or evaporation of the encapsulant. A formable, extrudable, cuttable mixture or dough is obtained by admixing ingredients comprising at least one plasticizable matrix material, the liquid encapsulant component, and at least one component for controlling the rate of release of the encapsulant. The admixing is performed under low shear and low temperature conditions to plasticize the plasticizable material without substantially destroying the encapsulant to obtain a substantially homogeneous plasticized viscoelastic, formable mixture. The liquid encapsulant component comprises an encapsulant and a liquid that acts as plasticizer. The liquid encapsulant component provides at least a substantial portion of the liquid plasticizer for forming the plasticized mixture.

Extrusion of the plasticized mixture may be performed without substantial expansion of the product thereby providing a high density product. The process of the present invention may be used to encapsulate heat sensitive components or readily oxidizable components, for example, pharmaceutically or biologically or nutritionally active components, without substantially destroying their activity. Examples of these may be enzymes, microorganisms or vitamins. The products of of the present invention may be edible for direct consumption or for incorporation into or addition to human food products or animal feed. In other embodiments of the invention, products, such as chemical or agricultural products such as pesticides, herbicides, fungicides, insecticides, rodenticides, or other products like detergents or flavorants, fragrances, and the like may be advantageously embedded or encapsulated to control or delay their release from their surrounding matrix.

In embodiments of the present invention, at least one additional ingredient or component may be used to control the release properties and hardness of the final product. The additional component may manage, control or affect the flow, diffusion or distribution of water or aqueous-based compositions into and within the final product particles. The additional ingredient or component for controlling the rate of release of the encapsulant may be a hydrophobic agent such as polyethylene, polyurethane, polypropylene, polyvinylchloride, polyvinylacetate, a fat, oil, wax, fatty acid, or emulsifier which increases the hydrophobicity of the matrix. The increased hydrophobicity helps to prevent or delays penetration of water or gastric juice into the matrix. Other ingredients which may be used to control the rate of the release are components which have a high water binding capacity which delay or prevent a fast dissolving of the matrix and thereby delay the release of the encapsulant into the matrix. Exemplary of high water binding capacity components which may be used are proteins, such as wheat gluten, gelatin, and casein, hydrocolloid gums, and the like.

In embodiments of the invention, matrix components may be added to increase the rate of release of the encapsulant. These release rate increasing components may dissolve more readily in water than does another matrix material. Upon dissolution, permeability of the particles is increased, thereby increasing access to the encapsulant by the penetrating aqueous-based solvent.

In accordance with the method of the present invention, at least one plasticizable, matrix-forming material such as durum wheat or semolina, vital wheat gluten, pregelatinized starch, flour, flour from cookies or crackers or flour from cookie or cracker type products, pentosans, or hydrocolloids which is at least substantially plasticizable by the liquid of the liquid encapsulant component at a temperature of less than about 50° C. is admixed with the liquid encapsulant component to obtain a formable mixture. An additional amount of a plasticizer such as water may be added to reduce or adjust viscosity of the mixture without the need to subsequently remove plasticizer prior to extrusion or forming. The encapsulant is admixed with the plasticizable matrix material under low temperature, low shear mixing conditions to distribute, coat, embed, or encapsulate the added active ingredient in the plasticized matrix material. Mixing is continued towards the extruder die while optionally adjusting the product temperature for sufficient formability.

The admixture is extruded through extrusion dies and cut or otherwise formed into pieces or pellets with no or substantially no expansion of the extrudate. The extrudate or pieces may then be dried and then surface treated with a film-building substance to coat the extruded pellets or pieces. The film-building substance may also contain additional components that delay or prevent the access of light, oxygen, and/or water to the matrix. In embodiments of the invention, one or more solid, pharmaceutically, nutritionally, biologically or, chemically active ingredients may be admixed with the plasticizable matrix material and liquid encapsulant component. The additional, optional solid encapsulant may be precoated with a coating material such as shellac, zein, chitosan, chitin, an emulsifier or the like to further control the release properties of the encapsulant from the matrix material.

The products of the present invention may be in the form of discrete particles, pellets, or tablets. They may be spherical in shape, curvilinear or lens-shaped, flat discs, oval shaped, or the like. The diameter of the particles may range from about 0.3 mm to about 7 mm and the l/d ratio may be from about 0.1 to about 10. The specific density of the pellets or particles may be from about 800 g/liter to about 1500 g/liter.

The total amount of plasticizer, such as water, admixed with the plasticizable matrix material, such as semolina or flour from ground cookies or ground crackers, to form a plasticized mass may range from about 20% by weight to about 50% by weight, preferably from about 25% by weight to about 45% by weight, based upon the weight of the matrix material such as semolina or flour from ground cookies or crackers. The liquid plasticizer content of the liquid encapsulant component may be at least about 35% by weight, generally at least about 50% by weight, based upon the weight of the liquid encapsulant component. The amount of the ingredient used to control the rate of release of the active component may range up to about 70% by weight, preferably from about 5% by weight to about 50% by weight, most preferably from about 10% by weight to about 35% by weight based upon the weight of the plasticizable matrix material such as semolina. The amount of the active component or encapsulant which may be encapsulated or embedded into the matrix may be from about 1% by weight to about 85% by weight, preferably from about 3% by weight to about 50% by weight, most preferably from about 5% by weight to about 30% by weight, based upon the weight of the plasticizable matrix ingredient such as semolina.

DETAILED DESCRIPTION OF THE INVENTION

A liquid encapsulant component which contains an active, sensitive encapsulant dissolved or dispersed in a liquid plasticizer is admixed with a plasticizable matrix material which is plasticizable by the liquid plasticizer to encapsulate the active encapsulant at a low temperature and under low shear conditions. Oil may be optionally added to the matrix material prior to adding the liquid encapsulant. In an embodiment of the invention, one or more plasticizable matrix materials and optional dry ingredients may be first dry mixed and subsequently mixed with oil. After mixing with oil, the liquid encapsulant component may be admixed into the matrix/oil preblend to obtain a mix. Before the mix forms a dough, it may be transferred to a compressing section of an extruder screw and extruded into discrete particles. The active component may be encapsulated and/or embedded in the plasticizable matrix component or material in a batch, semi-continuous, or continuous process to produce discrete, solid particles. The liquid content of the liquid encapsulant component provides substantially all or completely all of the liquid plasticizer needed to plasticize the matrix component to obtain a formable, extrudable, cuttable, mixture or dough. Removal of liquid plasticizer prior to extrusion to adjust the viscosity of the mixture for formability is not needed.

Release of an active component from the matrix may be purposely delayed or controlled over time so that the active component is delivered when and where it is needed to perform its intended function. The release of an active component from the matrix may be controlled by an additional ingredient or additive which affects the hydrophobicity of the matrix or particle, the water binding capacity of the matrix or particle, the solubility or porosity of the matrix material or particle, or the glass transition ($T_g$) of the matrix material or particle. Pre-process coating of an encapsulant prior to admixing it into the matrix material, extrusion process conditions, the final shape of the discrete particles, and optional coating of the discrete particles may also be used to control the release of an active component from the matrix material. The process of the present invention advantageously at least substantially uniformly distributes, embeds, or encapsulates an active component in the matrix material. The encapsulation process enhances stability of the active component against moist heat during further processing of the encapsulated active component, such as during pelletizing or extrusion. The active components may be dispersed in the matrix material on a microscopic or molecular level. Active components which are dispersed on a molecular level may provide a higher bioavailability when released, as compared to their crystalline forms. The active components in the final product may be encapsulated or embedded in either a shelf-stable solid form or liquid form. The encapsulants and encapsulated products of the present invention may be edible such as pharmaceutically or biologically or nutritionally active components, or flavors or fragrances or they may be inedible compositions such as a detergent, herbicide, fungicide, pesticide, insecticide, or rodenticide, and the like. They may be used for human or animal consumption. The encapsulants and encapsulated products may be suspensions of microorganisms in water, and suspensions or dispersions or emulsions or solutions of vitamins, enzymes, minerals or trace elements in water or other liquids. Release of an encapsulant from the matrix material may also be controlled by the use of a film or coating upon the discrete, solid matrix-encapsulated particles.

The plasticizable matrix material which is plasticizable at low temperatures by the liquid of the liquid encapsulant component may be a plasticizable biopolymer such as a carbohydrate, such as a starch or cyclodextrin, or polymer such as polyvinylpyrrolidone or other n-hydrophobic polymers such as copolymers of N-vinylpyrrolidone (NVP) and vinylacetate, polyvinyl alcohol, cellulose esters, cellulose ethers, and polyethylene glycol, pentosans, hydrocolloids such as carragenan, alginates, or gum arabic, wheat gluten, such as vital wheat gluten or isolated gluten, and mixtures thereof. Exemplary starches which may be used in the present invention are native or modified starches or pregelatinized starches derived from corn, wheat, rice, potato, tapioca, or high amylose starch. Sources of starch which may be used also include flours from grains such as corn, wheat, durum wheat, rice, barley, oat, or rye, and mixtures thereof. Preferred plasticizable matrix materials for edible products of the present invention are high gluten content flours, gluten from wheat, durum wheat or semolina, pregelatinized starch, pentosans, hydrocolloids, and mixtures thereof. For easier distribution or dispersibility in liquids such as water and oil, finely ground or powdered cookies or crackers, or ground cookie-like or cracker-like products may be employed as a matrix material. The ground cookie or cracker products may be obtained by grinding or milling cookies or crackers to obtain a particle size distribution similiar to that of a flour.

Durum products or ingredients which may be used in the present invention include durum semolina, durum granular, durum flour and mixtures thereof. Durum semolina is preferred. Durum semolina is the purified or isolated middlings of durum wheat prepared by grinding and bolting cleaned durum wheat to such fineness that when tested by the method prescribed in 21 CFR § 137.300(b)(2), it all passes through a No. 20 U.S. sieve, but not more than 3 percent passes through a No. 100 U.S. sieve. The semolina is freed from bran coat or bran coat and germ to such an extent that the percent of ash therein, calculated to a moisture-free basis, is not more than 0.92 percent. The durum granular product is a semolina to which flour has been added so that about 7% passes through the No. 100 U.S. sieve. Durum flour has not less than 98 percent passing through the No. 70 U.S. sieve.

Additional matrix components which may be used include solid components which are substantially non-plasticizable at temperatures lower than the decomposition temperature of the heat sensitive encapsulant. Exemplary of such optional, substantially non-plasticizable matrix components are at least substantially non-gelatinized starch, carbohydrates which have a lower molecular weight than starches, fiber, or other inert materials, such as cellulose, or hemi-cellulose. The lower molecular weight matrix components tend to dissolve more readily than does the starch and increase the penetrability or porosity of the matrix. As a result, access by the dissolution medium, such as water or acid, to the encapsulant is increased thereby permitting quicker release of the encapsulant from the matrix material. Examples of carbohydrates other than starch which may be used are sugars, such as mono- and di-saccharides, and starch hydrolyzate products such as dextrins or syrups with dextrose equivalent values (DE values) ranging from about 2 to about 99, or from about 5 to 98, and mixtures thereof.

The matrix material is used in an effective encapsulating amount. In embodiments of the present invention, the matrix material content, such as the semolina content or cookie or cracker flour content of the particles may be at least about 30% by weight, for example from about 60% by weight to about 95% by weight, based upon the weight of the final product.

The liquid plasticizer contained within the liquid encapsulant component is generally water but may be an aqueous-based composition such as a sugar solution, alcohol, glycerol, sorbitol, polyethylene glycol, polypropylene glycol, silicone, hexanol, pentanol, dimethylsulfoxide (DMSO), hexane, an oil, and mixtures thereof. The liquid encapsulant component provides at least a substantial portion or even the total amount of liquid plasticizer for forming a substantially homogeneous cohesive, plasticized, viscoelastic, formable mixture or dough. If the amount of liquid plasticizer, such as water, supplied by the liquid encapsulant component is not sufficient to obtain a formable mixture or dough at a sufficiently low temperature and under sufficiently low shear conditions so as to avoid substantial mechanical or thermal destruction of the plasticizable matrix material or encapsulant, then an additional amount of liquid plasticizer may be admixed with the other ingredients. The additional liquid plasticizer may be the same or different as the liquid plasticizer provided by the liquid encapsulant component. Exemplary total amounts of plasticizer, such as water, may range from about 20% by weight to about 70% by weight, preferably from about 25% by weight to about 45% by weight, based upon the weight of the plasticizable matrix material such as semolina.

The liquid plasticizer content of the liquid encapsulant component may be at least about 35% by weight, generally at least about 50% by weight, for example from about 65% by weight to about 90% by weight, based upon the weight of the liquid encapsulant component.

In embodiments of the invention, the formable mixture or dough may have a total plasticizer content, such as water, of about 10% by weight to about 50% by weight. The total plasticizer content may include water supplied by the liquid encapsulant component and additional plasticizer, such as glycerol, sorbitol or a combination thereof or any other liquids that enables the formation of a dough. Substantially higher plasticizer or moisture contents, such as for example well above 50% may result in a thin, low viscosity dough, that will either not be formable or the drying efforts would be unnecessary high. Substantially lower moisture contents, such as well below 5% may result in a dry product, which would be too fragile after forming and would fall apart. It also would generate frictional heat during extrusion forming which would be detrimental to the heat sensitive encapsulant. The water may be mixed with organic acids to adjust pH and to obtain a pleasant flavor in the final product.

For example, an aqueous dispersion of *Lactobacillus acidophilus* may have a moisture content of about 70/by weight and an encapsulant content (*Lactobacillus acidophilus*) of about 30% by weight. The 70% moisture content stemming from the acidophilus dispersion is used as a plasticizer. The ratio of wheat flour to moisture stemming from the aqueous encapsulant liquid may be about 3:1 to enable the formation of a homogeneous dough. Vegetable oil may be added to delay penetration of water into the matrix and delay the release of the microorganism.

The additional ingredients which may be used to control the release properties of the final product may be a hydrophobic agent for slowing down the rate of release of the encapsulant. Exemplary of components which may be added to affect the hydrophobicity of the matrix include fats, oils, waxes, fatty acids, emulsifiers, such as mono- or di-glycerides, synthetic polymers such as polyolefins such as polyethylene or polypropylene, polyvinyl chloride, polyvinyl acetate and derivatives thereof, paraffin, and modified starches from plant sources that possess hydrophobic properties that are obtained via either physical or chemical modification, and mixtures of hydrophobic components. Plant lipids or synthetic lipids with melting points up to about 65° C. may, for example, be employed as a hydrophobic agent. The hydrophobic components increase the hydrophobicity of the matrix and help to prevent or delay penetration of water or gastric juice into the matrix by repelling water or aqueous acids, thereby delaying the release of the encapsulant into the surrounding media.

Additional components which may be used to delay or prevent a fast release of the encapsulant from the matrix are components or agents which have a high water binding capacity. The agents may have a water binding capacity or water holding capacity which is greater than the water binding capacity of the matrix material, such as starch. The high water binding capacity component may bind water which penetrates the particles, or prevent the water from dissolving the matrix, thereby preventing or delaying the release of the encapsulant from the matrix. Exemplary of high water binding capacity agents which may be used in the present invention are protein from animal sources such as gelatin, casein, and protein from sources such as wheat, soy, corn, or other grains, and hydrocolloids such as carrageenans, alginates, xanthan gum, gum arabic, guar flour or guar gum, agar, tragacanth, karaya, locust bean gum, pectin, soluble fiber, insoluble fiber and the like. Exemplary proteins from grains which may be used are gluten, vital wheat gluten, zein, and soy protein concentrate. The proteins from plant sources may also be used to increase the tolerable addition of lipids within the matrix composition and thereby indirectly increase the hydrophobicity of the matrix. The high water binding capacity components may be used alone or mixtures thereof may be employed.

Process compatible additional components to facilitate processing, or to improve the taste, texture, or hydration behavior of the final pellets which may be employed include flavors, NaCl, nonfat dry milk, whey protein, high fructose corn syrup, leavening agents, lipids, such as oils or fats, chocolate liquor, chocolate, cocoa powder, compound coatings, concentrated fruit Juice, or particulates, such as ground nuts or almonds. The water may be pH adjusted to obtain a good tasting product. The addition of vegetable oil during mixing has been found useful to obtain a smooth continuous dough phase and it facilitates forming of the dough and cutting into discrete particles without sticking.

The additional components or ingredients, such as those used to control the rate of release of the encapsulant may be used in amounts up to about 70% by weight, preferably from about 5% by weight to about 50% by weight, most preferably from about 10% by weight to about 35% by weight, based upon the weight of the matrix material, such as semolina.

In addition to the encapsulant provided by the liquid encapsulant component, additional encapsulants in solid form may be included in the encapsulated products of the present invention. Active components which may be encapsulated or embedded in the matrixes in accordance with the present invention include pharmaceutical compositions or compounds, nutraceutical compositions or compounds, nutritional components, or biologically active components, flavorants, fragrances, detergents or surface-active compositions. The pharmaceutical compounds or compositions may, for example, include antibiotics, analgesics, vaccines, antiinflammatory agents, antidepressants, anti-viral agents, anti-tumor agents, enzyme inhibitors, formulations containing zidovudine, macromolecular polypeptides, aromatic nitro and nitroso compounds and their metabolites useful as anti-viral and anti-tumor agents, HIV protease inhibitors, viruses, and steroids, mixtures thereof, and the like.

Nutraceutical components may include components which promote health or prevent disease or enhance well-being such as antioxidants, phytochemicals, hormones, vitamins such as Vitamins A, B1, B2, B6, B12, C, D, E, K, pantothenate, folic acid, pro-vitamins, minerals such as calcium, selenium, magnesium salts, available iron, and iron salts, microorganisms such as bacteria, such as live *lactobacilli*, fungi, and yeast, prebiotics, probiotics, trace elements, essential and/or highly unsaturated fatty acids such as omega-3 fatty acids, and mid-chain triglycerides, nutritional supplements, enzymes such as amylases, proteases, lipases, pectinases, cellulases, hemicellulases, pentosanases, and phytases, pigments, oligopeptides, dipeptides, and amino acids, and mixtures thereof.

Biologically active components which may be encapsulated include agriculturally useful compositions to either prevent infestation such as herbicides, pesticides, insecticides, rodenticides, fungicides, mixtures thereof, and the like or to promote growth such as hormones, fertilizers, or other growth stimulating agents.

Exemplary of the active components which may be encapsulated or embedded in accordance with the present invention are: acepromazine, acetaminophen, acetohexamide, acetohydroxamic acid, acetylcholine, acetylcysteine acyclovir, albendazole, alclometasone dipropionate, allopurinol, alprazolam, alprostadil, amcinoide, amantadine, amdinocillin, amikacin amiloride, aminocaproic acid, aminophylline, aminosalicylate, aminosalicylic acid, amitriptyline hydrochloride, ammonium chloride, amobarbital, amodiaquine hydrochloride, amoxapine, amoxicillin, amphetamine sulfate, amphotericin, ampicillin amprolium, acetazolamide acetyldigoxin, acetylsalicylic acid, anileridine, anthralin, antipyrine, antivenin, apomorphine, apraclonidine, ascorbic acid, aspirin, acromycin atropine, amoxycillin anipamil, azaperone azatadine maleate, azathioprine, azithromycin, aztreonam, bacampicillin, bacitracin, baclofen, barium salts, beclomethasone diproionate, belladonna extract, bendroflumethiazide, benoxinate hydrochloride, benzethonium chloride, benzocaine, benzonatate benzthiazide, benztropine mesylate, betaine, betamethasone, betaxolol, betanechol chloride, biotin, biperiden, bisacodyl, bismuth, botulism antitoxin, bromocriptine mesylate, bromodiphenhydramine hydrochloride, bumetanide, bupivacaine, busulfan butabarbital sodium, butalbital, combinations of butalbital, caffeine and aspirin and codeine, beta-carotene, calcifediol, calcium carbonate, calcium citrate, calcium salts, candicidin, captopril, carbachol, carbamazepine, carbenicillin indanyl sodium, carbidopa, carbinoxamine maleate, carboprost tromethamine, carboxymethyl cellulose, carisoprodol, casanthranol, cascara, castor oil, cefaclor, cefadroxil, cefamandole nafate, cefazolin, cefixime, cefoperazone, cefotaxime, cefprozilu, ceftazidime, cefuroxime axetil, cephalexin, cephradine, chlorambucil, chloramphenicol, chlordiazepoxide, chloroquine phosphate, chlormadinone acetate, chlorthiazide, chlorpheniramine maleate, chloroxylenol, chlorpromazin, chlorpropamide, chlorprothixene, chlorprothixene, chlortetracycline bisulfate, chlortetracycline hydrochloride, chlorthalidone, chlorzoxazone, cholecalciferol, cholera vaccine, chromic chloride, chymotrypsin, cimetidine, cinoxazin, cinoxate, ciprofloxacin, cisplatin, clarithromycin, clavulanate potassium, clemastine fumarate, clidinium bromide, clindamycin hydrochloride, -palmitate and -phosphate, clioquinol, clofazimine, clofibrate, clomiphene citrate, clonazepam, cinnarizine, clonidine hydrochloride, clorsulon, clotrimazole, cloxacillin sodium, cyanocobalamin, cocaine, coccidioidin, cod liver oil, codeine, colchicine, colestipol, corticotropin, corisone acetate, cyclacillin, cyclizine hydrochloride, cyclobenzaprine hydrochloride, cyclophosphamide, cycloserine, cyclosporine, cyproheptadine hydrochloride, cysteine hydrochloride, danazol, dapsone, dehydrocholic acid, demeclocycline, desipramine, desoximetasone, desoxycorticosterone acetate, dexamethasone, dexchlorpheniramine maleate, dexpanthenol, dextroamphetamine, dextromethorphan, diazepam, diazoxide, dibucaine, dichlorphenamide, dicloxacillin sodium, dicyclomine, dienestrol, diethylpropion hydrochlorid, diethylstilbestrol, diflunisal, digitalis, dicoumarol, digitoxin, digoxin, dihydroergotamine, dihydrostreptomycin, dihydrotachysterol, dihydroxyaluminium amino acetate, dihydroxyaluminium sodium carbonate, diltiazem hydrochloride, dimenhydrinate, dimercaprol, diphenhydramine hydrochloride, diphenoxylate hydrochloride, diphteria antitoxin, dipyridamole, disopyramide phosphate, disulfiram, dobutamine hydrochloride, docusate calcium, docusate sodium, dopamine hydrochloride, doxepin hydrochloride, doxycycline, doxycycline hyclate, doxylamine cuccinate, dronabinol, droperidol, drotaverine, dydrogesterone, dyphylline, guaifenesin, enalapril maleate, analaprilat, ephedrine, epinephrine, equilin, ergocalciferol, ergoloid mesylates, ergonovine maleate, ergotamine tartrate, erythrityl tetranitrate, erythromycin, estradiol, estriol, estrogene, estrone, estropipate, ethcrynic acid, ethambutol hydrochloride, ethchlorvynol, ethinyl estradiol, ethionamide, ethopazine hydrochloride, ethotoin, ethynodiol diacetate, etidronate disodium, etoposide, eugenol, famotidine, fenoprofen, ferrous fumatate, ferrous gluconate, ferrous sulfate, flucytosine, fludrocortisone acetate, flunisolide, fluocinolone acetonide, fluocinonide, fluorescein sodium, fluorometolone, fluorouracil, fluoxymesterone, fluphenazine, flurandrenolide, flurazpam, flurbiprofen, folic acid, furazolidone, flunitrazepam, furosemide, gemfibrozil, gentamicin, gentian violet, glutarate, glutethimide, glycopyrrolate, chorionic gonadotropin, gramicidin, griseofulvin, guaifenesin, guanabenz, guanadrelsulfate, halazone, haloperidol, haloprogin, halothane, heparin calcium, hepatitis virus vaccine, hetacillin potassium, hexylresorcinol, histamine phosphate, histidine, homatropine, histoplasmin, hydralazine hydrochloride, hydrochlorothiazide, hydrocodone bitartrate, hydrocortisone, hexobarbital, hydroflumethiazide, hydromorphone hydrochloride, hydroquinone, hydroxocobalamin, hydroxyamphetamine, hydroxychloroquine sulfate, hydroxyprogesterone caproate, hydroxyurea, hydroxine hydrochloride, hydroxine pamoate, hyoscyamine, hyoscyamine sulfate, ibuprofen, ifosfamide, imipramide, imipramide hydrochloride, indapamide, indomethacin, insulin, inulin, iocetamid, iodoquinol, iohexol, iopamidol, ipecac, ipodate calcium, ipodate sodium, isocarboxacid, isoetharine hydrochloride, isoflurane, isoniacid, isopropamide iodine, isoproterenol hydrochloride, isosorbide dinitrate, isotretenoin, isoxsuprine hydrochloride, kanamycin sulfate, ketoprofen, ketoconazole, labetalol hydrochloride, lanolin, leucine, leucovorin calcium, levamisole hydrochloride, levocarnithine, levodopa, levonorgestrel, levorphanol tartrate, levothyroxine sodium, lidocaine, lincomycin hydrochloride, lindane, liothyronine sodium, liotrix, lisinopril, lithium carbonate, loperamide hydrochloride, loracarbef, lonetil, lorazepam, lovastatin, loxapine, lysine, mafenide acetate, magaldrte, magnesium carbonate, magnesiumchloride, magnesium gluconate, magnesium oxide, other magnesium salts, malathinon, manganese salts, manganese, maprotiline hydrochloride, mazindol, measle virus vaccine, mebendazole, mebrofenin, mecamylamine hydrochloride, meclizine hydrochloride, meclocycline, meclofenamate sodium, medroxyprogesterone acetate, mefenamic acid, megestrol acetate, meglumine, melphalan, menadiol sodium diphosphate, menadione, menotropine, meperidine, mephenyloin, mephobarbital, meprednisone, meprobamate, mercaptopurine, mesoridazine besylate, mestranol, metaproterenol sulfate, metaraminol bitartrate, methacycline hydrochloride, methadone hydrochloride, methamphetamine hydrochloride, methazolamide, methdilazine, methenamine, methicillin sodium, methimazole, methionine, methocarbamol, methotrexate, methoxsalen, methoxyflurane, methsuximide, methyclothiazide, methylbenzethonium chloride, methyldopa, methylergonovine maleate, methylphenidate hydrochloride, methylprednisolone, methyltestosterone, methysergide maleate, metoclopramide, metolazone, meoprolol tartrate, metronidazole, metyrapone, metyrosine, mexiletine hydrochloride, mexiletine hydrochloride, miconazole, minocycline hydrochloride, minoxidil, mitomycin, mitotane, molindone hydrochloride, monobenzone, morphine sulfate, mupirocin, medazepam, mefruside, methandrostenolone, methylsulfadiazine, nadolol, nafcillin, nafcillin sodium, nalidixic acid, nalorphine, naloxone, nandrolone decanoate, nandrolone phenpropionate, naproxen, natamycin, neomycin, neomycin sulfate, neostimine bromide, niacin, nitrofurantoin, nalidixic acid, nifedipine, nitrazepam, nitrofurantoin, nitroglycerine, nitromerson, nizatidine, nonoxynol 9, norethindrone, norethindrone acetate, norfloxacin, norgestrel, nortriptyline hydrochloride, noscapine, novobiocin sodium, nystatin, opium, oxacillin sodium, oxamniquine, oxandrolone, oxazepam, oxprenolol hydrochloride, oxtriphylline, oxybenzone, oxybutynin chloride, oxycodone hydrochloride, oxycodone, oxymetazoline hydrochloride, oxymetholone, oxymorphone hydrochloride, oxyphenbutazone, oxytetracycline, padimate, panreatin, pancrelipase, papain, panthenol, papaverin hydrochloride, parachlorophenol, paramethasone acetate, paregoric, paromomycin sulfate, penicillamine, penicillin, penicillin derivatives, pentaerythritol tetranitrate, pentazocine, pentazocine hydrochloride, pentazocine salts, pentobarbital sodium, perphenazine, pertussis, phenacemide, phenazopyridine hydrochloride, phendimetrazine tartrate, phenelzine sulfate, phenmetrazine hydrochloride, phenobarbital, phenophtalein, phenoxybenzamine hydrochloride, phentermine hydrochloride, phenylalanine, phenylbutazone, phenylephrine hydrochloride, phenylpropanolamine hydrochloride, physostigmine, phytonadione, pilocarpine, pimozide, pindolol, piperazine, piroxicam plicamycin, poliovirus vaccine inactivated, polycarbophil, polymycin b sulfate, polythiazide, potassium chloride, potassium citrate, potassium cluconate, potassium iodine, potassium sodium tartrate, povidone iodine, pralidoxime chloride, pramoxine hydrochloride, pramezam, prazepam, praziquantel, prazosin hydrochloride, prazosin hydrochloride, prednisolone, prilocalne, primaquine, primidone, probenecid, probucol, procainamide hydrochlorid, procaine hydrochloride, procarbacine hydrochloride, prochlorperazine, prochlorperazine maleate, procyclidine hydrochloride, progesterone, proline, promazine, promazine hydrochloride, promazine, promethazine, promethazine hydrochloride, propafenone hydrochloride, propantheline, proparacaine hydrochloride, propoxycaine hydrochloride, propoxyphene hydrochloride, propoxyphene napsylate, propanolol hydrochloride, propyliodone, propylthiouracil, propylthiouracil, protriptyline hydrochloride, pseudoephedrine hydrochloride, pumice, pyrantel pamoate, pyrazinamide, pyrethrum extract, pyridostigmine bromide, pyridoxine hydrochloride, pyrilamine maleate, pyrimethamine, pyroxylin, pyrvinium pamoate, phenacetin, phenyloin, prednisone, uinidinegluconate, quinidine sulfate, rabies vaccine, racepinephrine ranitidine, rauwolfia serpentina, resorcinol, ribavirin, riboflavin, rifampin, ritodrine, rubella virus vaccine, saccharin, saccharin sodium, salicylamide, salicylic acid, salsalata, scopolamine, secobarbital sodium, selenius acid, selenium sulfate, sennaserine, simethicone, sodium ascorbate, sodium bicarbonate, sodium fluoride, sodium gluconate, sodium iodide, sodium lactate, sodium nitrite, sodium ditroprusside, sodium salicylate, spironolactone, stannozolol, streptomycin, sucralfate, sulfacetamide, sulfadiazine, reserpine, sulfadioxine, sulfamerazine, sulfamethazine, sulfamethizole, sulfamethoxazole, sulfamethoxydiazine, sulfapyridin, sulfasalazine, sulfaperin, sulfathiazole, sulfisoxazole, sulfinpyrazone, sulindac, suprofen, stilains, tamoxifen citrate, temacepam, terbutaline sulfate, terfenadine, terpin, testolacton, testosterone, tolazamide, tolbutamide, tetracaine, tetracycline, tetrahydrocycline, theophylline, thiabendazole, thiamine hydrochloride, thiamin, thiamylal, thiethylperazine thimerosal, thioguanine , thioridazine hydrochloride, thistrepton, thiotepa, thiothixene, threonine, thyroid, ticarcillin, timolol, tioconazole, titaniumdioxide, tolazamide, tolbutamide, tolmetin, tolnaftate, trazodone hydrochloride, tretinoin, triacetin, triamcinolone, triamterene, triazolam, trichorfon, trichlornethiazide, trientine hydrochloride, trifluoperazine hydrochloride, triflupromazine, trihexyphenidyl hydrochloride, trimeprazine tartrate, trimethadione, trimethobenzamide hydrochloride, trimethoprim, trioxsalen, tripelennamine, triprolidine, trisulfapyrimidine, tropicamide, trypsin, tryptohan, tuberculin, tyloxapol, tyropanoate sodium, tyrosine, tyrothricin, thyrothricin bethamethasone, thiotic acid, sotalol, salbutamol, norfenefrine, silymarin, dihydroergotamine, buflomedil, etofibrate, indometacin, urea, valine, valproic acid, vancomycin hydrochloride, vasopressin, verapramil, vidarabine, vinblastine, vincristine, vitanins, warfarin, yellow fever vaccine, zinc acetate, zinc carbonate, zinc chloride, zinc gluconate, beta acetyl digoxin, piroxicam, haloperidol, ISMN, amitriptylin, diclofenac, nifedipine, verapamil, pyritinol, nitrendipin, doxycycline, bromhexine, methylprdnisolone, clonidine, fenofibrate, allopurinol, pirenyepine, levothyroxin, tamoxifen, metildigoxin, o-(beta-hydroxyethyl)-rutoside, propicillin, aciclovir mononitrate, paracetamol, naftidrofuryl, pentoxifylline, propafenone, acebutolol, L-thyroxin, tramadol, bromocriptine, loperamide, ketotifen, fenoterol, cadobelisate, propanolol, enalaprilhydrogen maleate, bezafebrate, ISDN, gallopamil, xantinol nicotinate, digitoxin, flunitrazepam, bencyclane, dexapanthenol, pindolol, lorazepam, diltiazem, piracetam, phenoxymethylpenicillin, furosemide, bromazepam, flunarizin, erythromycin, metoclopramide, acemetacin, ranitidin, biperiden, metamizole, doxepin, dipotassium chloroazepate, tetrazepam, estramustine phosphate, terbutaline, captopril, maprotiline, prazosin, atenolol, glibenclamide, cefaclor, etilfrine, cimetidine, theophylline, hydromorphone, ibuprofen, primidone, clobazam, oxaceprol, medroxyprogesterone, flecainid, pyridoxal 5 phosphate glutaminate, hymechromone, etofylline clofibrate, vincamine, cinnarizine, diazepam, ketoprofen, flupentixol, molsimine, glibornuride, dimetinden, melperone, soquinolol, dihydrocodeine, clomethiazole, clemastine, glisoxepide, kallidinogenase, oxyfedrine, baclofen, carboxymethylcysteine, thioridazine, betahistine, L-tryptophan, murtol, bromelaine, prenylamine, salazosulfapyridine, astemizol, sulpiride, benzerazide, dibenzepine, acetylsalicylic acid, miconazol, nystatin, ketoconazole, sodium picosulfate, coltyramine, gemfibrocil, rifampicin, fluocortolone, mexiletin, amoxicillin, terfenadrin, mucopolysaccharide polysulfade, triazolam, mianserin, tiaprofenic acid, amezinium metilsulfate, mefloquine, probucol, quinidine, carbamazepine, L-aspartate, penbutolol, piretanide, aescin amitriptyline, cyproterone, sodium valproinate, mebeverine, bisacodyl, 5-aminosalicylic acid, dihydralazine, magaldrate, phenprocoumon, amantadine, naproxen, carteolol, famotidine, methyldopa, auranofine, estriol, nadolol, levomepromazine, doxorubicin, medofenoxate, azathioprine, flutamide, norfloxacin, fendiline, prajmalium bitartrate, lipid derivatives of phosphonatides, amphiphilic polymers, adenosine derivatives, sulfated tannins, monoclonal antibodies, and metal complexes of water soluble texathyrin.

The amount of the active component or encapsulant which is incorporated into the products of the present invention may be such so as to provide or deliver an effective amount, such as a pharmaceutically effective amount or a nutraceutically effective amount of the active component at its intended location, such as the small intestine. Exemplary amounts of the active component or encapsulant which may be encapsulated or embedded into the matrix may be from about 1% by weight to about 85% by weight, preferably from about 3% by weight to about 50% by weight, most preferably from about 5% by weight to about 30%/by weight, based upon the weight of the matrix ingredient, such as semolina.

Film-building or film-forming substances which may be used to coat encapsulants prior to incorporation into the matrix include commonly used coating materials such as zein, pectin, shellac, gelatin, fats, oils, waxes, emulsifiers, native or modified starch, chitosan, chitin, and mixtures thereof. The film-building or film-forming substance may also be used to coat the extruded, particulate product. Pretreatment of the encapsulant by coating it with a film forming substance such as a high melting fat or wax, or with an emulsifier such as glycerin monostearate, or the like, tends to prevent unwanted interaction between an encapsulant and the matrix. The encapsulants and the extrudate particles may be coated with film-forming amounts of the substances in aqueous or alcoholic solutions, or oleaginous compositions.

In embodiments of the invention pellets may be coated in a two step coating process. After discrete particles have been cut at an extrusion die, the substantially undried pellets may be coated with a first component of a composite coat, such as an acetic-acid-chitosan-solution. After this step a second coat may be applied using a gel forming counter ion, such as a polyphosphate solution, that causes the chitosan to gel and form a chitin coat. The second ion may also be provided by a pectin and the resulting composite coat may then be a pectin-chitin coacervate.

The film-forming substances or coatings may also contain additional components that protect the particulates or pellets, or encapsulant, from the influence of light, such as titanium dioxide, or cocoa-based products. The coatings may also contain anti-oxidants to protect the pellets or encapsulants from the influence of oxygen or air.

In accordance with embodiments of the present invention, the thickness of the coating upon the encapsulant may be used to control the rate of release of encapsulant once the dissolving media, such as water, reaches the encapsulant. For example, increasing the thickness of the coating on the encapsulant slows its rate of release into the media. Also, increasing the thickness of the coating on the extrudate or pellet delays release of the encapsulant from the matrix material. In embodiments of the invention, the amount of coating may range from about 0.5% to about 50% by weight, based on weight of the total product, depending upon the desired release of the encapsulant.

In accordance with the method of the present invention, all of ingredients may be admixed together at a temperature of about 5° C. to about 50° C., for example about 30° C. to obtain a formable mixture or dough. Mixing or dough temperatures substantially higher than about 50° C. are undesirable, because any fat or oil in the formula tends to separate, or the heat sensitive substances to be encapsulated and embedded would be destroyed. Temperatures much lower than room temperatures, such as for example 0° C. are for most purposes impractical but may be employed in special applications. In embodiments of the invention, the temperature may be adjusted by external heating, below 50° C. so as to facilitate forming and enable cutting without the material sticking to the cutter.

In embodiments of the present invention, external heating of the ingredients during their admixture is not required. For example, where durum wheat is used as the plasticizable matrix material, heating of the durum wheat and water to cook or gelatinize the durum wheat may not be needed to obtain an uncooked pasta-type product.

The admixing of the ingredients is conducted under low shear mixing conditions without substantially destroying or decomposing the matrix material or encapsulant. An overall quantitative measure of the shear used inside an extruder, for example, is the specific mechanical energy input. In embodiments of the present invention, the specific mechanical input during admixing of the ingredients to obtain a formable mixture or dough may be below about 150 Wh/kg, preferably below about 100 Whkg, and most preferably below about 50 Wh/kg.

In embodiments of the invention, the pressure under which the formable mixture or dough may be formed may range from about 1 bar, preferably from about 5 bars to about 100 bars.

The at least one additional ingredient or component, such as the hydrophobic component, or high water binding capacity component for controlling the release properties of the final product, may be dry blended or preblended with the plasticizable matrix material such as semolina. In other embodiments of the invention, the additional component for controlling the release properties may be added separately.

In embodiments of the invention, a dough comprising all ingredients may be made using conventional batch or continuous mixers. Subsequently, the dough, which may be a crumbly dough may be fed into a single screw extruder. The single screw extruder presses the dough against a die plate and plasticizes the crumbs into a continuous dough phase which may then be pressed through an extrusion die and subsequently cut into individual particulates.

In other embodiments of the invention, the dough can be made continuously and using a continuous mixer or extruder alone. Twin screw extruders or co-rotating twin screw mixers may be advantageously used which enable the steps of continuously mixing the dough and subsequently extruding the dough through an extrusion die plate. Co-rotating intermeshing twin screw extruders, such as those available from Buhler, Switzerland, Clextral France, Werner and Pfleiderer Germany, APV England or Wenger USA, or a Co-Kneader, available from Buss, Switzerland may be employed For feeding solid components to an extruder, conventional solids feeding devices such as a volumetric or gravimetric feeder may be used. Liquid injection nozzles may be used for injecting liquid active components or solutions, dispersions, emulsions or suspensions. In embodiments of the invention, a side feeder and liquid injection nozzles may be employed. If an injection nozzle is used, the pressure for injecting the liquid encapsulant should be sufficiently higher than the pressure in the extruder so that the encapsulant can be injected into the extruder barrel. For example, if the pressure of the plasticized mass inside the extruder is 10 bars, the injection pressure may be about 2 to about 5 bars higher, i.e. 12 to 15 bars.

In embodiments where an encapsulant is pre-coated with a film-building material or coating material, the coating material may be applied in conventional manner such as by spraying or enrobing using conventional coating equipment. Commercially available pre-coated active ingredients, such as precoated minerals or vitamins may be employed.

The admixing of the added active ingredients or encapsulants inside the extruder may be accomplished by using an appropriate extrusion screw configuration for achieving low shear mixing. For example, a combination of alternating small pitch conveying elements with distributive mixing elements, that are staggered at an angle to each other for providing axially oriented leakage flow inside the extruder barrel may be employed. The combination of alternating conveying elements with distributive mixing elements cause the material flow to be continuously interrupted without shearing of the mass thus resulting in mixing of the material at low mechanical energy input.

In other embodiments of the invention, other extruder screw configurations may be used that facilitate low shear distributive mixing, such as screw elements of the type ZME, TME, SME, and so-called IGEL elements commercially available from Werner and Pfleiderer.

The total length of the distributive mixing section may be about 3 to 12 l/d, preferably about 4 to 6 l/d to sufficiently admix and distribute and embed or encapsulate the added active components in the matrix.

The at least substantially homogeneous mixture of matrix material and added active ingredient or encapsulant may then be conveyed towards an extruder die plate. The conveying may be achieved by the use of low pitch extruder screw conveying elements which build up sufficient pressure prior to extruding the mix so that it can be forced through the apertures in the die plate. Another function of the low pitch elements is that they increase the degree of fill inside the last extruder barrel section. The increased degree of fill enables control of the temperature profile of the mix inside the extruder barrel for achieving optimum viscosity adjustment and extrusion through the subsequent die openings.

Critical is the rate of extrudate per die area, which should be less than about 5 kg/h per $mm^2$, preferably less than 3 kg/h per $mm^2$ and most preferably less than about 0.5 kg/h per $mm^2$. High rates will result in high shear rates inside the die that will cause increased viscous dissipation, pressure and temperatures which may adversely affect the encapsulant and may lead to unwanted product expansion.

The extrudate rope may be cut at the die face using a rotating cutter, pelletizer, or rotating knives. In other embodiments, the extrudate rope may be cut away from the die using conventional cutting or forming means for producing pellets or tablets. The cut pieces, pellets, or tablets, may have a length:diameter ratio (l/d ratio) of about 0.5 to 10, preferably about 1.

In accordance with the process of the present invention, the particle size may be varied to control the surface to volume ratio of the pellets or pieces for achieving a desired controlled release of the encapsulant. The particle size may be varied, for example, by the use of different diameters for the extrusion die openings. Particle size may also be varied by the use of a variable speed cutter either at the die plate at the end of the extruder or away from the extruder after the ropes have been conveyed for a short distance. By varying the speed of the cutter, the size of the cut pieces may be varied for a given extruder throughput. The use of a variable cutter which is spaced a short distance from the die plate, for example, between about 0.5 meters to about 5 meters permits further surface cooling, further surface drying, and reduced stickiness to provide better cutting of the ropes into pellets.

In producing products for human or animal consumption, variation of particle size to control the surface to volume ratio of the pellets is critical for achieving a controlled release of the encapsulant during passage of the pellets or particles through the mouth, the stomach, and the intestine. Variation of particle size is also critical for controlling the residence time of the pellets inside the stomach. For example, particles smaller than 1 mm pass through the stomach or intestine faster than would particles larger than for example 2.5 mm.

After cutting, the resulting pieces or pellets may be dried to a sufficiently low moisture content which assures a sufficiently prolonged storage stability or shelf life. For example, the pellets may be dried to achieve a storage stability or shelf life of at least about six months, preferably at least about twelve months, most preferably at least about thirty-six months. In embodiments of the present invention, the drying may be performed using conventional drying equipment using drying temperatures which do not adversely affect the thermal stability of the encapsulants. Exemplary drying temperatures may range from about 10° C. to about 50° C. The drying may be conducted to achieve a moisture content of less than about 30% by weight, preferably less than about 12% by weight, most preferably less than about 10% by weight. In embodiments where no starch or substantially no starch is used as a matrix material, the moisture content may be less than about 6% by weight.

The product may be dried using a conventional fluidized bed or other conventional drying means. The product may be optionally coated after drying using conventional coating equipment such as coating pans, coating drums, or spray devices.

In embodiments where film-building substances or coatings are applied to the particles or pellets, conventional spray nozzles may be located close to the die or for spraying an aqueous or alcoholic solution of the film-building substances onto the cut pieces as they fall downwardly from the extruder die. In other embodiments, the film-building substances may be applied after drying of the pellets. For example, the film-building substances may be applied using spray nozzles, conventionally known fluid bed coating apparatus, or other conventional coating apparatus and methods. If the application of the film-building substances increases the moisture content above a shelf stable level, the water or other volatile media may be removed from the surface of the particles by additional drying.

In embodiments of the present invention, the extruded pieces or pellets may be compressed in conventional tablet presses to obtain compressed versions of the extruded pellets.

In other embodiments of the present invention, the mixture may be extruded through a sheeting die into a sheet. The extruded sheet may then be cut or molded into individual pieces, such as tablets, or disks, using a rotary die or rotary cutter, or reciprocating cutter or counterrotating drums conventionally known as agglomeration drums or tabletting drums.

The products of the present invention may possess a dense, granular structure. They may comprise discrete particles which may be spherical, lens-shaped, or flat discs having diameters of from about 0.5 mm to about 7 mm, preferably from about 0.5 mm to about 5 mm, most preferably from about 1 mm to about 3 mm, exclusive of any optional exterior film-building substances or coatings. In embodiments of the invention, the particles of the invention may be in the form of tablets with diameters of up to about 10 mm. The length-to-diameter ratio (l/d) of the particles may be from about 0.1 to about 10, for example about 0.5 to about 2, preferably about 1. The particles are generally uniform in size, dense, and granular to increase palatability to humans and animals in a substantially compact form that is easy to swallow without chewing. They are non-expanded, and exhibit a non-puffed, substantially non-cellular, dense structure. The starch component of the matrices may be substantially ungelatinized or at least partially gelatinized, and not substantially destructurized or dextrinized. Exemplary specific densities of the products of the present invention are between about 800 g/liter and about 1500 g/liter (about 0.8 to about 1.5 g/cm$^3$).

The encapsulated products of the present invention may be incorporated with or without grinding into foods intended for human or animal consumption such as baked goods, for example, bread, wafers, cookies, crackers, pretzels, pizza, and rolls, ready-to-eat breakfast cereals, hot cereals, pasta products, snacks such as fruit snacks, salty snacks, grain snacks, and microwave popcorn, dairy products such as yoghurt, cheese, and ice cream, sweet goods such as hard candy, soft candy, and chocolate, beverages, animal feed, pet foods such as dog food and cat food, aqua-culture foods such as fish food and shrimp feed, and special purpose foods such as baby food, infant formulas, hospital food, medical food, sports food, performance food or nutritional bars, or fortified foods, food preblends or mixes for home or food service use, such as preblends for soups or gravy, dessert mixes, dinner mixes, baking mixes such as bread mixes, and cake mixes, and baking flour.

In preferred embodiments, the active encapsulant is either a live microorganism, enzyme, microneutrient, trace element, nutraceutical component, biologically active material or a combination thereof. The encapsulated product may be redispersed as a liquid, or as a solid for human food, animal feed, or pharmaceutical purposes. The products of the present invention may be used as or incorporated into foods for special purposes, such as performance foods, mood foods, medical foods, nutritional supplements, sport foods, baby foods, toddler foods, infant foods, or foods for pharmaceutical purposes or other dietetic purposes. The discrete particulates or granules of the present invention may be used as a topping for breakfast cereals, snacks, soups, salad, cakes, cookies, crackers, puddings, desserts or ice cream. They may also be used as a granular ingredient for yogurts, desserts, puddings, custards, ice cream or other pasty or creamy foods. Regularly sized pieces may be individually packaged or used as nutritional snacks or, for example added to nutritional food in bar form.

The present invention is further illustrated by the following non-limiting examples where all parts, percentages, proportions, and ratios are by weight, and all temperatures are in ° C. unless otherwise indicated:

EXAMPLE 1

Example of an Encapsulated and Protected Enzyme Continuous Process:

A dry matrix blend consisting of 70 parts semolina and 25 parts wheat gluten was fed into a feed port of a Werner & Pfleiderer twin screw extruder at a rate of 2.5 kg/hr. Vegetable oil was fed at a rate of 0.29 kg/hr and water at a rate of 0.06 kg/hr into the same barrel of the twin screw extruder. Liquid encapsulant (about 70 wt./o water), comprising the enzyme phytase and water, was fed at a rate of 0.82 kg/hr into the same port of the twin screw extruder. All barrels of the extruder were kept at a temperature of 21° C. The die consisted of 40 circular openings, each 0.5 mm in diameter. At a screw speed of 67 rpm, the above ingredients were mixed, conveyed and formed into a dough that was extruded through the die openings at a pressure of 92 bar and a product temperature of 39° C. On a calculated basis, the rate of extrudate per die area is 0.468 kg/hr per mm$^2$. Upon exiting the die, the exiting ropes were cut with rotating knives into discrete particles of 0.5–1.5 mm length and air dried for about 30 minutes. The resulting pellets contain encapsulated and protected active enzyme.

EXAMPLE 2

Example of an Encapsulated and Protected Enzyme, Batch Process:

A matrix blend consisting of 58 parts semolina and 6 parts wheat gluten was preblended and mixed with 11 parts of vegetable oil in a mixer for 3 minutes. Then 22 parts of liquid encapsulant comprising the enzyme phytase and subsequently 3 parts water were added and mixed for 12 minutes to obtain a blend. The blend was then extruded through extrusion dies having a diameter of about 0.65 mm using a single screw extruder. The blend was formed into a dough that was extruded at about 90 bar and at a temperature of about 37° C. Upon exiting the die, the product was cut with rotating knives into discrete particles of about 0.5 mm to about 1 mm in length and air dried for about 30 minutes. The resulting pellets contain encapsulated enzyme.

EXAMPLE 3

Example of an Encapsulated and Protected *Lactobacillus:*

A dry matrix blend consisting of 70 parts semolina and 25 parts wheat gluten may be fed into a feed port of a Werner & Pfleiderer twin screw extruder at a rate of 2.5 kg/hr. Vegetable oil may be fed at a rate of 0.29 kg/hr and water at a rate of 0.06 kg/hr into the same barrel of the twin screw extruder. Liquid encapsulant (about 80 wt. % water), comprising the microorganism *lactobacillus acidophilus* and water, may be fed at a rate of 0.82 kg/hr into the same port of the twin screw extruder. All barrels of the extruder may be kept at a temperature of 21° C. The die may have 40 circular openings, each 0.5 mm in diameter. At a screw speed of 67 rpm, the above ingredients may be mixed, conveyed and formed into a dough and extruded through the die openings at a product temperature of less than 40° C. On a calculated basis, the rate of extrudate per die area is 0.468 kg/hr per mm²Upon exiting the die, the existing ropes may be cut with rotating knives into discrete particles of 0.5–1.5 mm length and dried for about 30 minutes either in a vacuum drier or under CO2 or another inert gas to prevent the access of oxygen. The resulting pellets contain encapsulated and protected active live microorganisms.

EXAMPLE 4

Example of an Encapsulated and Protected Enzyme, Batch Process:

68 parts semolina were preblended and mixed with 11 parts of vegetable oil in a mixer for 3 minutes. Then, 14 parts of liquid encapsulant comprising about 20% of the enzyme phytase and 80% water and subsequently 7 parts water were added and mixed for 12 minutes to obtain a blend. The blend was then extruded at 60 rpm. The extrusion temperature was about 37° C. Upon exiting the die, the product was cut into discrete particles and dried at 35° C. to about 6% moisture. The resulting pellets contain encapsulated enzyme. The loss of enzyme activity after encapsulation was less than 5%, based upon the enzyme activity units per gram of added enzyme.

What is claimed is:

1. An encapsulated product comprising a substantially homogeneous mixture of:
    at least one plasticized matrix material comprising a durum ingredient, wherein the amount of said at least one plasticized matrix material is at least about 30% by weight, based upon the weight of the encapsulated product;
    about 1% by weight to about 85% by weight of an encapsulant, based upon the weight of the matrix material, wherein the encapsulant is at least substantially uniformly distributed in said at least one plasticized matrix material, said encapsulant being at least one component selected from the group consisting of a pharmaceutical component, neutraceutical component, nutritional component, fragrance component, and biologically active component; and
    a hydrophobic agent for controlling the rate of release of the encapsulant, the amount of hydrophobic agent being about 10% to about 70% by weight, based upon the weight of the at least one plasticizable matrix material,
    wherein said encapsulated product is in substantially non-expanded, particulate form.

2. An encapsulated product as claimed in claim 1 wherein said encapsulant comprises at least one member selected from the group consisting of enzymes and live microorganisms.

3. An encapsulated product according to claim 1, wherein said encapsulant is at least one member selected from the group consisting of antioxidants, phytochemicals, hormones, microorganisms, prebiotics, probiotics, enzymes, formulations containing zidovudine, macromolecular polypeptides, aromatic nitro and nitroso compounds and their metabolites useful as anti-viral and anti tumor agents, HIV protease inhibitors, antibiotics, viruses, steroids, oligopeptides, amino acids, fragrance components, adenosine derivatives, sulfated tannins, monoclonal antibodies, and metal complexes of water-soluble texathyrin.

4. A food topping comprising an encapsulated product according to claim 1 in granular form.

5. An encapsulated product as claimed in claim 1 wherein the encapsulated product is obtained from a formable mixture which is extruded through a die having multiple apertures, at a rate of extrudate per die area of less than about 5 kg/h per mm².

6. An encapsulated product as claimed in claim 5, wherein the rates of extrudate per die area is less than 3 kg/h per mm².

7. An encapsulated product as claimed in claim 6, wherein the rate of extrudate per die area is less than about 0.5 kg/h per mm².

8. An encapsulated product as claimed in claim 5, wherein the diameter of the apertures is from about 0.3 mm to about 5 mm.

9. An encapsulated product as claimed in claim 5, wherein the diameter of the apertures is from about 0.5 mm to about 1 mm.

10. An encapsulated product as claimed in claim 5, wherein the diameter of the apertures is from about 0.3 mm to about 5 mm.

11. An encapsulated product according to claim 5 wherein said formable mixture is extruded by a single screw or twin screw extruder.

12. An encapsulated product according to claim 5 wherein said formable mixture is obtained by admixing ingredients in an extruder and the formable mixture is extruded from the extruder to obtain pieces.

13. An encapsulated product ac according to claim 1, wherein the hydrophobic agent is selected from the group consisting of fats, oils, waxes, fatty acids, and synthetic polymers.

14. An encapsulated product according to claim 1, wherein the hydrophobic agent comprises an oil.

15. An encapsulated product comprising a substantially homogeneous mixture of:
    at least one plasticized matrix material comprising a durum ingredient, wherein the amount of said at least one plasticized matrix material is at least about 30% by weight, based upon the weight of the encapsulated product;
    about 1% by weight to about 85% by weight of an encapsulant, based upon the weight of the matrix material wherein the encapsulant comprises live *lactobacilli* and is at least substantially uniformly distributed in said at one plasticized matrix material; and
    a hydrophobic agent for controlling the rate of release of the encapsulant, wherein said encapsulated product is in substantially non-expanded, particulate form.

16. An encapsulated product according to claim 1, wherein a liquid encapsulant component comprising the encapsulant and a liquid plasticizer provides at least a substantial portion of liquid plasticizer for plasticizing at least one plasticizable matrix material.

17. An encapsulated product according to claim 1, comprising about 10% to about 35% by weight of the hydrophobic agent, based upon the weight of the at least one plasticizable matrix material.

18. An encapsulated product according to claim 1, wherein the durum ingredient is selected from the group consisting of at least one of durum semolina, durum granular, and durum flour.

19. An encapsulated product as claimed in claim 1 comprising about 3% by weight to about 50% by weight of the encapsulant, based upon the weight of the matrix material.

20. An encapsulated product as claimed in claim 1 comprising about 5% by weight to about 30% by weight of the encapsulant, based upon the weight of the matrix material.

21. An encapsulated product as claimed in claim 1, wherein the amount of said at least one plasticized matrix material is from about 60% by weight to about 95% by weight, based upon the weight of the encapsulated product.

22. An encapsulated product as claimed in claim 3, wherein the amount of said at least one plasticized matrix material is from about 60% by weight to about 95% by weight, based upon the weight of the encapsulated product.

* * * * *

UNITED STATES PATENT AND TRADEMARK OFFICE
CERTIFICATE OF CORRECTION

| | | |
|---|---|---|
| PATENT NO. | : 7,201,923 B1 | Page 1 of 1 |
| APPLICATION NO. | : 09/233443 | |
| DATED | : April 10, 2007 | |
| INVENTOR(S) | : Bernhard H. van Lengerich | |

It is certified that error appears in the above-identified patent and that said Letters Patent is hereby corrected as shown below:

On the Title page, Related U.S. Application Data, Item (60), third line, of the printed patent, after "Oct. 9, 1998" please insert --, provisional application no. 60/079,060, filed on March 23, 1998--.

At column 1, line 9, after "Nos." please insert --60/079,060 filed on March 23, 1998,--.

Signed and Sealed this
Twenty-ninth Day of January, 2013

David J. Kappos
*Director of the United States Patent and Trademark Office*